(12) United States Patent
Cheng et al.

(10) Patent No.: US 7,193,774 B2
(45) Date of Patent: Mar. 20, 2007

(54) SUB-DIFFRACTION LIMIT RESOLUTION IN MICROSCOPY

(75) Inventors: Ming Cheng, Tucson, AZ (US); Weinong Chen, Tucson, AZ (US)

(73) Assignee: The Arizona Board of Regents on Behalf of the University of Arizona, Phoenix, AZ (US)

( * ) Notice: Subject to any disclaimer, the term of this patent is extended or adjusted under 35 U.S.C. 154(b) by 0 days.

(21) Appl. No.: 11/001,104

(22) Filed: Dec. 1, 2004

(65) Prior Publication Data

US 2005/0117206 A1 Jun. 2, 2005

Related U.S. Application Data

(60) Provisional application No. 60/526,375, filed on Dec. 2, 2003.

(51) Int. Cl.
*G02B 21/06* (2006.01)
*G02B 21/00* (2006.01)

(52) U.S. Cl. ........................ 359/386; 359/368; 359/385

(58) Field of Classification Search ........ 359/356–390, 359/227–236, 738–740, 558, 566
See application file for complete search history.

(56) References Cited

U.S. PATENT DOCUMENTS

| 4,255,014 | A | * | 3/1981 | Ellis | 359/371 |
| 5,420,717 | A | * | 5/1995 | Tabata | 359/371 |
| 5,889,276 | A | * | 3/1999 | Yonezawa et al. | 250/201.3 |
| 5,966,204 | A |  | 10/1999 | Abe | 356/51 |
| 6,025,956 | A | * | 2/2000 | Nagano et al. | 359/386 |
| 6,600,598 | B1 | * | 7/2003 | Piekos | 359/385 |
| 6,643,061 | B2 | * | 11/2003 | Osa et al. | 359/385 |
| 6,891,671 | B1 | * | 5/2005 | Greenberg | 359/388 |
| 6,924,893 | B2 | * | 8/2005 | Oldenbourg et al. | 356/369 |

OTHER PUBLICATIONS

"Review Indentation Fracture: Principles and Applications" Lawn et al., Journal of Materials Science, 10, 1975, p. 1049-1081.
"Optimization of Electrolyte Material for use in Solid Oxide Electrolysis Cells" Brach, Thesis 2000, pp. 1-78.
"Near-Field Scanning Optical Microscopy" Dunn, Chem. Rev. 1999, 99, p. 2891-2927.
"Dynamic Vickers Indentaion of Brittle Materials" Anton et al., Wear 239, 2000, p. 27-35.
"Direct Observation and Analysis of Indentation Cracking in Glasses and Ceramics" Cook et al., Journal Am. Ceram. Soc., 73, 1990, p. 787-817.
"Vickers Indentation Fracture Toughness Test Part 1 Review of Literature and Formulation of Standardised Indentation Toughness Equations" Ponton et al., Materials Science and Technology, vol. 5, 1989, pp. 865-872.

(Continued)

*Primary Examiner*—Thong Q Nguyen
(74) *Attorney, Agent, or Firm*—Hayes Soloway P.C.

(57) ABSTRACT

A method and apparatus for visualizing sub-micron size particles employs a polarizing microscope wherein a focused beam of polarized light is projected onto a target, and a portion of the illuminating light is blocked from reaching the specimen, whereby to produce a shadow region, and projecting diffracted light from the target onto the shadow region.

11 Claims, 6 Drawing Sheets

A close-up view of specimen stage and eyepiece of the modified microscope. The solid lines represent unobstructed beams, and the dashed lines are diffracted beams from the object (crack line).

OTHER PUBLICATIONS

"Vickers Indentation Fracture Toughness Test Part 2 Application and Critical Evaluation of Standardised Indentation Toughness Equations" Ponton et al., Materials Science and Technology, vol. 5, 1989, p. 961-976.

"Strength and Toughness of Tape-Cast Yttria-Stabilized Zirconia" Selcuk et al., Journal Am. Ceram. Soc., 83, 2000, p. 2029-2035.

"Experimental Method for a Dynamic Biaxial Flexural Strength Test of Thin Ceramic Substrates" Cheng et al., Journal Am. Ceram. Soc., 85, 2002, p. 1203-1209.

"Light Principles and Experiments" G. Monk, Second edition, p. 77.

"Handbook of Biological Confocal Microscopy" J. Pawley, p. 15-26.

"Evaluation of KIC of Brittle Solids by the Indentation Method with Low Crack-to-Indent Ratios" Niibara et al., Journal of Materials Science Letters 1, 1982, pp. 13-16.

"Standard Test Method for Vickers Indentation Hardness of Advanced Ceramics" ASTM International Designation: C 1327-03, p. 465-472.

"Geometrical and Physical Optics" R.S. Longhurst, p. 338-340.

* cited by examiner

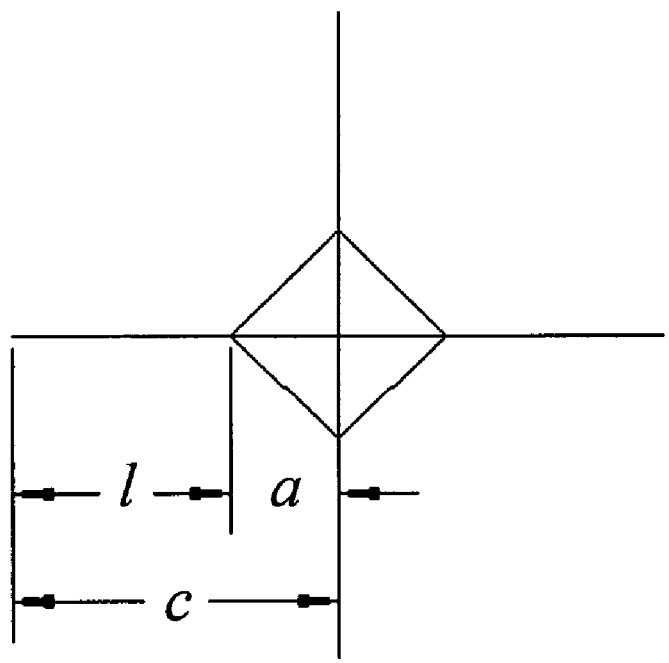
Figure 1. Plane view of Vickers indentation with radial cracks.

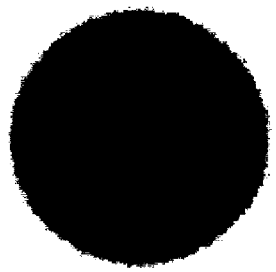
Figure 2. The distribution pattern in an Airy Discs.
(website: http://glinda.lrsm.upenn.edu/~weeks/confocal/)

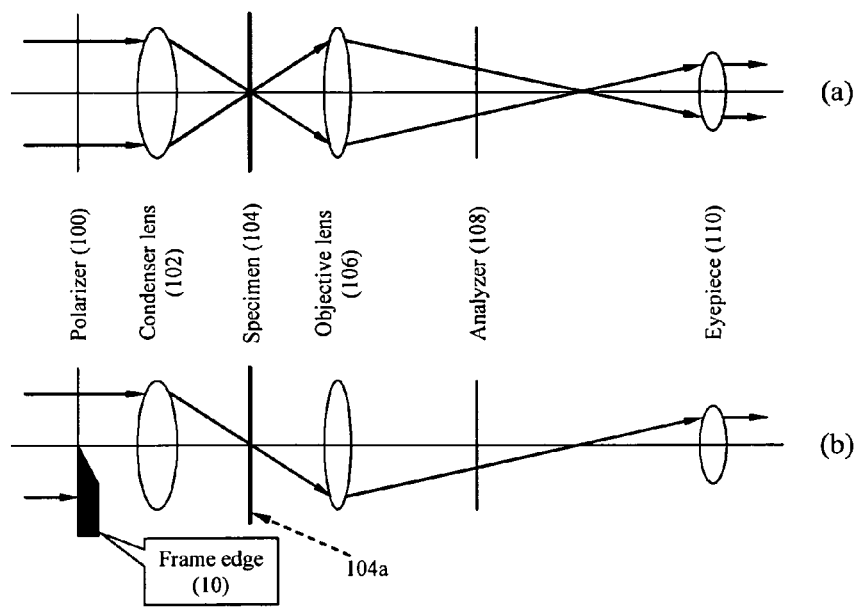
Figure 3. (a) Conventional polarizing microscope; (b) modified microscope with a frame edge positioned at the middle of the field of view. The optical systems are simplified and the illumination optical paths (Condenser lenses) are unfolded schematically for clarity.

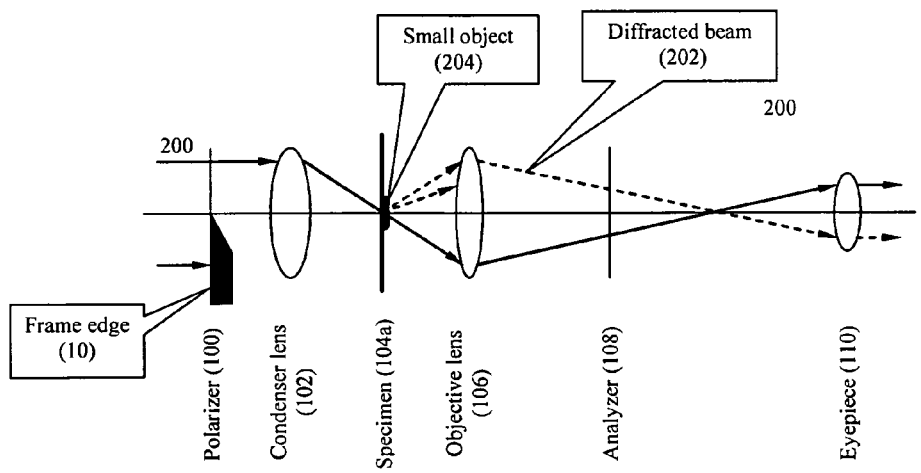
Figure 4. A close-up view of specimen stage and eyepiece of the modified microscope. The solid lines represent unobstructed beams, and the dashed lines are diffracted beams from the object (crack line).

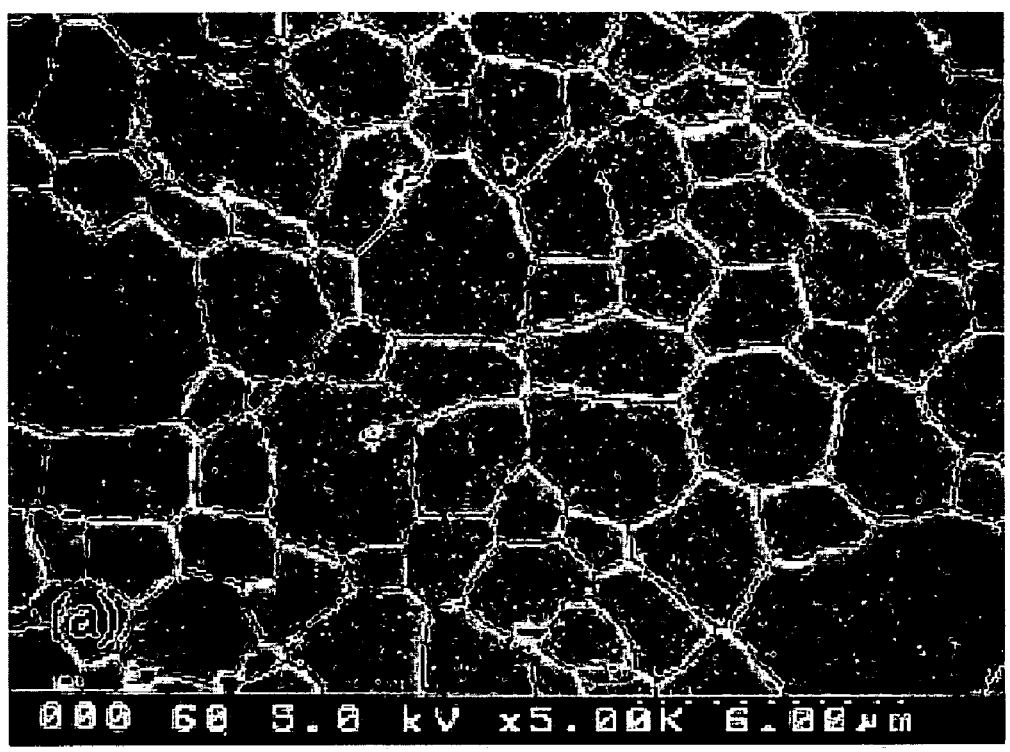
Figure 5. SEM micrograph of pure 8YSZ.

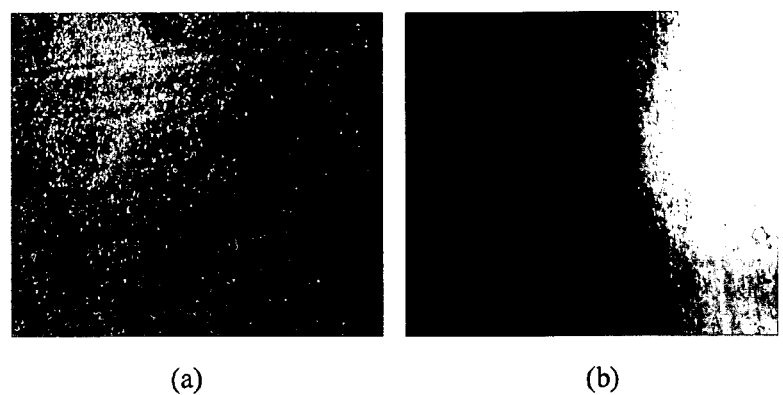
Figure 6. Vickers indentation on an 8YSZ specimen at about 300x magnification. (a) without shadow, (b) with shadow introduced from left by the frame edge.

SUB-DIFFRACTION LIMIT RESOLUTION IN MICROSCOPY

CROSS REFERENCE TO RELATED APPLICATION

The following application claims priority to provisional patent application 60/526,375 filed on Dec. 2, 2003.

GOVERNMENT RIGHTS

The United States Government may have certain rights in this invention pursuant to NASA Grant # NAG8-1469.

BACKGROUND OF THE INVENTION

1. Field of the Invention

The following invention relates to sub-diffraction limit resolution in microscopy. The invention has particular utility in the use of microscopy in the testing of fracture toughness of thin ceramic substrates and will be described in connection with such utility, although other utilities such as measuring sub-micron size particles including biological particles.

2. Description of the Prior Art

Indentation techniques are well developed for hardness study. The American Society of Testing and Materials (ASTM) developed a standard test method for Vickers indentation hardness of advanced ceramics (ASTM C 1327-96a, 1996) incorporated herein by reference. Vickers indentation techniques have also been widely used for studying fracture toughness of brittle materials such as glass and ceramics since surface crack traces were first recognized as indicative of fracture toughness by Palmqvist in 1957. These crack traces are referred to as indention traces or Palmqvist cracks.

In general, the procedure of the Vickers indentation toughness test includes producing an indentation on a plane surface of the material under investigation by a standard hardness tester and subsequently studying the induced cracks by a microscope. It is important to note that indentation is considered micro when the applied indenter load is less than 5N, otherwise, indentation is called macro indentation.

With the measured data of the indenter, load, and the dimensions of the induced cracks, it is possible to evaluate the toughness of the material. For example, a Vickers hardness tester usually makes a diamond indentation with cracks emanating from the diamond corners as shown in FIG. 1. For most mathematical models based on the Vickers hardness tester and published in the literature, the c/a or l/a ratio depicted in FIG. 1 was limited to a certain range. For example, Niihara et al (1982) proposed an equation that requires the l/a ratio to be between 0.25 and 2.5.

The advantages of the Vickers indentation toughness technique are the simplicity and cost effectiveness of the measurement procedure. The specimen preparation is also relatively simple, requiring only a flat surface. And, at least 10 tests can be performed on a surface of only 100 mm$^2$. The disadvantage of this technique is that an accurate measurement of the crack length c or l, usually measured under an optical microscope, is difficult. The indentation induced cracks are often hard, if not impossible, to observe because the width of indentation-induced cracks is very narrow, especially near the crack tips that the indention-induced cracks are beyond the resolution of common optical microscopes. Although measurements of the indention induced cracks can be conducted under a scanning electronic microscope (SEM), the usage of a SEM will significantly slow down the experimental procedure and greatly increase experiment costs.

Also, ordinary optical microscopes are limited in resolving power, and therefore cannot observe smaller indention cracks using light diffraction. Even assuming an optical system is perfect, because of the wave property of the light, the smallest spot resolvable by an optical microscope is ultimately defined by the diffraction of the illuminating light. At a small enough scale, physical optics principles take effect, i.e., the wave-like motion of light will deflect around corners of an object under observation to a tiny but finite degree. This phenomenon is known as the "diffraction limit" of an optical microscope. For example, suppose two point sources of light are to be imaged by a microscope. Because of light diffraction the two point sources of light will be imaged by a microscope as two discs of light distribution. These discs are each referred to as an Airy Disc, i.e., a high irradiance circular spot. FIG. 2 shows graphically a light distribution pattern of an Airy Disc of a point source due to light diffracting from an object under observation.

As shown in FIG. 2, the Airy Disc consists of a central bright peak surrounded by a set of concentric dark and light rings. The resolution limit of a microscope is defined as the distance of the two point sources at which their images has a separation so that the peak of one Airy Disc coincides with the first dark ring of the other. This is referred to as the Rayleigh's Criterion for resolution. The numerical expression of Rayleigh's Criterion is as follows:

$$d = 1.22 \frac{\lambda f}{D} = 0.61 \frac{\lambda}{N.A.} \qquad (1)$$

where d is the smallest distance between two objects resolvable by a microscope, $\lambda$ is the wavelength of light, f is the focal length of the microscope's objective lens, D is the diameter of the aperture of the microscope, and N.A. is the numerical aperture of the microscope (Smith, 1966).

Using Eq. (1), a numerical value of the resolution imposed by the diffraction limit can be calculated. For example, for a modem microscope objective lens having a N.A. of 1.3, assuming that the illumination light has a wavelength of 400 nm, the smallest object the microscope can resolve is 200 nm. However, it is desirable to be able to optically observe objects smaller than that scale.

Several designs have been invented to overcome the aforementioned problem with microscopes available in the art. Among them are confocal microscopes with a spatial resolution of 200 nm (Pawley, 1995), and near-field scanning microscopes with a spatial resolution of 60 nm (Dunn, R. C., 1999). There is also an older technique in optical microscopy called dark-field microscope, which is capable of observing particles of the size as small as 5 nm (Monk, 1963).

Outside the field of microscopy, there also exist several ways to observe structures with dimensions smaller than the diffraction limited scale. In optical testing, a Foucault knife-edge method is commonly used to find defects as small as one tenth of the wavelength $\lambda/10$ (e.g. 40 nm, using blue light illumination at 400 nm) in an optical component, such as a mirror surface. In this technique, an illuminated pinhole and a sharp knife-edge are located in the same plane away from the mirror (e.g. a spherical concave mirror) being tested. If the mirror surface is perfectly spherical and free of any defect, then an image of the pinhole will be formed with a uniform light distribution. When the knife-edge is moved across the line of light at the image point, a uniform shadow can be observed to cross the surface of the mirror. However, if very small surface defects exist on the mirror, these defects will cause the light impinged upon them to diffract and subsequently deform the spherical wave of the incident light. Now an observer behind the knife-edge will see light spots (diffraction patterns from the defects) on the dark shadow when the knife-edge is moved across the field (Longhurst, 1973). This technique resembles the method used in dark-field microscope, in which the direct illuminating light beam is obstructed and only half of the diffraction orders from the small particles are observed. Furthermore, an extension of the Foucault knife-edge, or the Schlieren method, is used to detect small variation of refractive index in a medium. The Schlieren method has been applied to fluid dynamics to study the behavior of a moving fluid (Longhurst, 1973).

In addition, to solve some of the above problems with microscopy, some researchers focused on the observability of indention cracks. Ponton and Rawlings (Ponton and Rawlings, 1989b) proposed a method where a minimum indenter load of about 50 N produces visible cracks so that accurate measurement of the indention cracks under common optical microscope. These macro-hardness testers have dominated the art because they ensure cracks produced by the Vickers hardness tester could be measured, and micro indentation was believed to produce no indentation cracking (Anton and Subhash, 2000). Other researchers have focused on improving the observability of indentation cracks produced using Vickers hardness testers by polishing the surface of the test specimens. The specimen surfaces were usually polished to at least 1 µm diamond finish (Ponton and Rawlings, 1989b). Although Ponton and Rawlings pointed out that processes such as polishing, could produce residual stresses on the surface to prevent correct test results (Ponton and Rawlings, 1989b), polishing seemed to be a necessary process for specimen preparation reported in the literature.

However, most of the prior art mathematical models are based on the assumption that there are no pre-existing surface stresses on test specimens. Although proper heat treatment could remove the stresses created by polishing; it may change the physical properties of the test specimen. Other prior art methods proposed to deal with the problems associated with these pre-existing stresses on specimens by highlighting the pre-existing surface cracks using a fluorescent dye penetrant (Ponton and Rawlings, 1989). However, these methods produce side effects, such as extra post-indentation slow crack growth in many ceramics, thereby preventing an accurate evaluation of the specimen's toughness.

There are other problems with the above mentioned methods of indention testing. Thin ceramic substrates are widely used as electrolytes in solid oxide electrolyzers, and are typically made by a tape-cast process. After sintering, the products are usually in the form of thin sheets with a typical thickness 0.5 mm or less in engineering applications. As a result, indenter load of 50 N tends to break the specimen substrates. In practice, the majority of the ceramic substrates with this thickness can only be indented by micro-indentation.

Other researchers in the art, Cook and Pharr (1990), found that a radial crack forms extremely early (possibly almost instantly) in the loading process (typically 0.8 N). Small cracks caused by such loads can not possibly be detected by the conventional optical methods described above. In addition, many thin ceramic substrates are used with an as-fired surface finish. Polishing of such surfaces would alter the actual fracture toughness of the substrates. However, leaving the surface of the substrate unpolished introduces even more difficulties in the observation and measurement of small cracks.

Thus, a better technique for measuring indentation cracks in thin substrates is needed.

SUMMARY OF THE INVENTION

The present invention provides a system, i.e., method and apparatus for sub-diffraction limit resolution by modification of a conventional polarizing microscope by obstructing a portion of the illuminating beam upstream of the condenser lens whereby to produce a shadow or dark background or region upon which diffracted light from the target may be projected.

BRIEF DESCRIPTION OF THE DRAWINGS

Further features and advantages of the present invention will be seen from the following detailed description taken in conjunction with the accompanying drawings wherever like numerals depict like parts, and wherein:

FIG. 1 shows a diamond pattern produced from a Vickers hardness tester with measured cracks;

FIG. 2 shows graphically a light distribution pattern of an Airy Disc of a point source due to light diffracting from an object under observation;

FIGS. 3(a) and 3(b) illustrate the optical path of a light beam when a conventional polarizing microscope and method are used to evaluate a sample and the optical path of a light beam (FIG. 3(a)), and when an exemplary microscope and method of the invention are used for the observation of the sub micron cracks (FIG. 3(b)), respectively;

FIG. 4 shows in detail the optical path of a light beam for an unobstructed part of the beam and a diffracted part of the beam in a microscope employing the exemplary method of the invention;

FIG. 5 is an SEM micrograph of pure 8YSZ for use in an experiment employing the exemplary method of the invention; and FIGS. 6(a) and 6(b) show a Vickers indentation on an 8YSZ specimen at about 300× magnification without a shadow (FIG. 6(a)) and with a shadow (FIG. 6(b)), respectively.

DETAILED DESCRIPTION OF THE INVENTION

The instant invention provides a system for achieving sub-diffraction limit resolution in microscopy by a modification of a conventional polarizing microscope. More particularly, in accordance with the present invention a portion of the illuminating beam to a polarizing microscope is obscured upstream of the condenser lens as to produce a shadow or dark background upon which diffracted light from the target is projected.

FIG. 3(a) illustrates the optical paths of a conventional polarizing microscope and FIG. 3(b) a modification permitting the observation of the micro-indentation cracks consistent with an embodiment of the instant invention respectively. Both the conventional polarizing microscope and the polarizing microscope of the instant invention include a polarizer 100, a condenser lens 102, a specimen stage 104, an objective lens 106, and analyzer 108 and an eyepiece 110.

In the conventional polarizing microscope, a light beam (depicted by arrows) passes through the polarizer 100, where the light beam is plane polarized, to condenser lens 102. The condenser lens 102 focuses the light beam onto the specimen stage 104. At the specimen stage 104, the light beam is separated into individual wave components that are each polarized in separate, but perpendicular planes i.e., "extraordinary rays". The extraordinary rays then pass through the objective lens 106, where magnification occurs, to the analyzer 108. The analyzer 108 polarizes light at a 90 degree angle from the polarizer, and if no specimen is present, the field will become black. However, if a specimen is placed on the specimen stage 104, the extraordinary rays will be polarized by the analyzer, where the recombined light beam will be passed to the eyepiece. Light rays will then emerge from the eyepiece parallel from each other, and the specimen will appear bright or colored.

In the polarizing microscope of the instant invention the polarizer 100 includes a frame edge 10 positioned at the middle of the field of view for the microscope, and a rotating specimen stage 104*a*. The frame edge 10 obstructs half of the illuminating light beam. This obstruction produces two effects. First, it generates an oblique, incident beam on the specimen under observation e.g., a crack line, and part of this oblique light beam is diffracted by the crack line. Second, the shadow of the frame edge provides a dark background to see the diffracted light from the crack line (if no crack is seen, the specimen stage may be rotated and/or moved). The combination of these two effects makes it possible to observe features with sub diffraction-limit resolution.

FIG. 4 shows in detail the optical ray trace of the unobstructed part of illuminating beam 200, i.e., the solid lines, and the diffracted beam 202, i.e., the dashed lines, from a sub-micron object or target 204, e.g., an indention crack in accordance with the present invention. As is shown in FIG. 4, half of the light beam passes through the polarizer 100, where the light is polarized, to the condenser lens 102. From the condenser lens 102, the light beam then passes to the sub-micron sized object or target 204, where part of the illuminating beam is diffracted off the sub-micron sized object or target and into the darkened region. Thus, an image of the sub-micron sized object or target against a dark background is produced when the sub-micron sized object or target is viewed from an eyepiece.

As can be seen from FIG. 4, generally, two geometrical conditions are met for this system to work optimally: (1) the object needs to be located in the vicinity of the shadow line made by the frame edge; and (2) the object needs to be able to cause diffraction into the dark region. This entails it having structural components parallel to the edge of the frame edge. The first condition specifies the size of the observation range. The second requirement presents a limitation on the observable structural feature of the object. However, this limitation can be overcome by making two orthogonal images of the same object and superimposing them to form a complete picture.

Experiments and Test Results

Thin (0.76 mm in thickness) specimens of 8-mol % yttria stabilized zirconia (8YSZ) were made from TZ-8YSZ powder (from Tosoh, Japan). The powder was then processed into a slurry with dispersant, binder, and plasticizer, and the slurry was tape-cast. The specimens were laser-cut out of green sheets and sintered at 1450° C. for 3 hours (Cheng, Chen and Sridhar, 2002). The surface flatness of as-fired specimens was between 20 and 30 μm as measured by a microscope. FIG. 5 is a SEM picture showing the microstructure of this material. An intersection method was used to estimate the average grain size, i.e., lines were drawn on the SEM pictures, with the distance between two grain-boundaries being measured along the lines. The average grain size of pure 8YSZ is found from FIG. 5 to be 2.1 μm.

A micro Vickers indentation was made with a MICROMET®3 micro hardness tester, which is a product of BUEHLER LTD. The indenter load applied was 4.91 N-which was determined by trial and error to ensure a c/a ratio within the required range. The half-diagonal length (a) of the indentation was measured directly by the light microscope attached to the hardness tester.

To determine the crack length, a polarizing metallurgical microscope (Zeiss Model IM 35) was used to measure the total length (2c) of the induced crack on the ceramic sheet specimen. The characteristics of the crack are as follows: length of the crack typical 80 μm and width of the crack 40 nm, as measured by a scanning electron microscope (Hitachi, Model S-2460N). These cracks were not visible under the normal working condition of the Zeiss microscope at 300× magnification (FIG. 6(*a*)). When the magnification was switched to 1000×, the image could no longer be properly focused due to the surface roughness. Therefore, it was impossible to observe any cracks by this microscope in normal operation mode. However, using the method of this invention, the expected cracks could be observed. The crack line became clearly visible when the opaque frame of the polarizer of the polarizing microscope was moved to near the center of the observing field with the shadow of the polarizer frame being near the location of the crack line, as shown in FIG. 6(*b*).

The above method was repeated using a BUEHLER® metallurgical microscope (BUEHLER® VERSAMET 3 METALLOGRAPH) and the same effect was observed. The only visible crack line was the one parallel to the shadow cast by the frame. Crack lines perpendicular to the frame edge were not visible because the incident light was only being diffracted in the bright region, producing a small signal in a very noisy background. Thus, the diffracted beam could not reach the dark region to be observed.

Two thin 8YSZ ceramic substrates were tested using the above method and apparatus, and over 30 tests were performed on each substrate. With the indenter loads and the dimensions of indentation and the resultant cracks, the test results were processed to obtain fracture toughness values using the following equations (Selçuk and Atkinson, 2000).

$$K_{IC} = 0.035 \frac{H_V a}{\phi} \left(\frac{E\phi}{H_V}\right)^{\frac{2}{5}} \left(\frac{l}{a}\right)^{-\frac{1}{2}} \text{ for } 0.25 \le \frac{l}{a} \le 2.5 \quad (2)$$

$$K_{IC} = 0.0143 \left(\frac{E}{H_V}\right)^{\frac{2}{3}} \left(\frac{p}{c^{\frac{3}{2}}}\right) \left(\frac{l}{a}\right)^{-\frac{1}{2}} \text{ for } 1 \le \frac{l}{a} \le 2.5 \quad (3)$$

$$K_{IC} = 0.055 \frac{H_V a^{\frac{1}{2}}}{\phi} \left(\frac{E\phi}{H_V}\right)^{0.4} \log_{10}\left(\frac{8.4a}{c}\right) \quad (4)$$

and $$K_{IC} = H_V a^{\frac{1}{2}} \left(\frac{E}{H_V}\right)^{\frac{2}{5}} (10^F) \quad (5)$$

where E is the Young's modulus, Hv is the Vickers hardness, Φ is a dimensionless constant taken to be 2.7, P is the applied load, a is the half length of the indenter diagonal, c is the crack length from the center of the indent, and l is the crack length from the corner of the indent. In Eq. (5), $$F = -1.59 - 0.34x - 2.02x^2 + 11.23x^3 - 24.97x^4 + 16.32x^5 \quad (6)$$

where $x = \log_{10}(c/a)$.

The reason for selecting these four equations is not only because they have been reported to be valid for the Palmqvist-type cracks and more accurate in determining toughness than others, but also that these equations have been used by Selçuk and Atkinson (2000) to evaluate the toughness of the same material using macro indentation toughness evaluation methods. Thus, it is possible to compare the test results from different sources using different methods.

The Young's modulus used in Equations (2)–(5) to evaluate toughness values was 216 GPa. This is in concurrence with the Young's modulus of 8YSZ ceramic material as reported by Selçuk and Atkinson (2000). The fracture toughness results reduced from the experiments using the method of this invention are shown in Table 1. The results by Selçuk and Atkinson (2000) are also listed in Table 1 for comparison. The test results are statistically stable as evidenced by the small standard deviations. The specimens A and B can be considered identical in properties since they were made from one green tape with the same processing parameters. The tests on specimens A and B were conducted at different times intentionally for the purpose of avoiding perspective errors. Tests on specimen A were about one week later than those on specimen B. it is shown from Table 1 that the differences of the measurements of the average toughness between specimen A and specimen B are 0.53% by Eq. (2), 6.09% by Eq. (3), 1.61% by Eq. (4) and 2.27% by Eq. (5). The number of tests on specimen A and B were more than 30 each. Equation (2) shows the minimum standard deviation among these four equations whereas Eq. (3) shows the maximum standard deviation. In comparison with the toughness measurement results from Selçuk and Atkinson (2000) as shown in Table 1, the micro indentation toughness evaluation results obtained using the system of this invention are comparable with the results obtained by macro indentation evaluation methods. It should be noted that the system of this invention is more versatile and can be applied on thin or small specimens where macro indentation is not applicable.

TABLE 1

Fracture toughness (KIC, MPa · m1/2) measured by micro Vikers indentation at ambient temperature for 8YSZ

| Equation | Selçuk and Atkinson | | Specimen A | | Specimen B | |
|---|---|---|---|---|---|---|
| | KIC | std | KIC | Std | KIC | Std |
| Equation (2) | 1.85 | 0.11 | 1.89 | 0.06 | 1.90 | 0.10 |
| Equation (3) | 1.50 | 0.18 | 1.15 | 0.12 | 1.22 | 0.21 |
| Equation (4) | 1.85 | 0.09 | 1.86 | 0.09 | 1.89 | 0.13 |
| Equation (5) | 1.80 | 0.08 | 1.76 | 0.10 | 1.80 | 0.16 |

To investigate the effects of surface polishing on the toughness values, another group of micro Vickers indentation toughness evaluation tests were performed on a surface-polished but otherwise the same specimen. The test results, which are listed in Table 2, confirmed that the surface polishing could significantly change the test results. The tests were conducted on a specimen with the same surface condition as that in practical service; otherwise, the specimen must be rigorously heat treated to recover the surface condition.

TABLE 2

Fracture toughness values ($K_{IC}$, MPa · m$^{1/2}$) of 8YSZ with different surface machining finish measured by micro Vickers indentation technique oat ambient temperature

| State | Equation (2) | | Equation (3) | | Equation (4) | | Equation (5) | |
|---|---|---|---|---|---|---|---|---|
| | $K_{IC}$ | std. | $K_{IC}$ | std. | $K_{IC}$ | std. | $K_{IC}$ | std. |
| As-fired | 1.90 | 0.10 | 1.22 | 0.21 | 1.89 | 0.13 | 1.80 | 0.16 |
| Polished | 2.22 | 0.20 | 1.99 | 0.58 | 2.25 | 0.17 | 2.21 | 0.16 |

Thus, if the SEM measurements are assumed to be an accurate determination of crack length, the experimental results using the system of the present invention show that the error of measurement was within 5%. Thus, it is possible to use the system of this invention with a conventional microscope to evaluate the toughness of thin ceramic substrates, even substrates with as-fired surface conditions.

Further, specimens of 8YSZ material were tested using the system of the present invention. The experimental results are comparable to the results from literature, corroborating the validity of the present invention. Experiments with surface-polishing specimens indicated that the polishing procedure increased the toughness measurement results significantly. Thus, the present invention provides an efficient method and apparatus and economical method and apparatus to measure small crack dimensions on thin ceramic substrate surfaces, either polished or as-fired.

While the invention has been described in connection with measuring of small crack, i.e., sub-micron size dimensions on thin ceramic substrate surfaces the invention also advantageously may be used for detecting and for measuring sub-micron sized particles such as mold, dust, and various biological particles including weaponized bio-agents. A particular feature and advantage of the present invention is that the invention permits resolution to 40 nm (equivalent to $\lambda/10$ in visible wavelength), using a conventional polarizing microscope with minimal, low-cost modification.

REFERENCES

Anton, R. J. and Subhash, G., 2000. Dynamic Vickers Indentation of Brittle Materials. Wear, Vol. 239, 27–35.

ASTM C 1327–96a, 1996. Standard Test Method for Vickers Indentation Hardness of Advanced Ceramics. American Society of Testing and Materials Annual Book of Standards, 15.01, 543–47.

Brach, S., 2000. Optimization of Electrolyte Material for Use in Solid Oxide Electrolysis Cells. Master's thesis, University of Ariz. Tucson.

Cheng, M., Chen, W. and Sridhar, K. R., 2002. Experimental Method for a Dynamic Biaxial Flexural Strength Test of Thin Ceramic Substrates. Journal of the American Ceramic Society, Vol. 85[5], 1203–209.

Cook, R. F. and Pharr, G. M., 1990. Direct Observation and Analysis of Indentation Cracking in Glass and Ceramics. Journal of the American Ceramic Society, Vol. 73, 787–817.

Dunn, R. C., 1999. Near-Field Scanning Optical Microscopy. Invited review article for *Chemical Reviews*, Vol. 99, 289 1–2927.

Longhurst, R. S., 1973. Geometrical and Physical Optics. Longman.

Monk, G. S., 1963. Light Principles and Experiments. pp. 77, Dover. Niihara, K., Morena, R., and Hasselman, D. P. H., 1982. Journal of Materials Science Letters, Vol. 1, 13–16.

Palmqvist, 1957. A Method to Determine the Toughness of Brittle Materials, Especially Hard Metals. (in Swed.), *Jernkontorets Ann.,* 141, 303–07.

Ponton, C. B. and Rawlings, R. D., 1989a. Vickers Indentation Fracture Toughness Test, Part 1. Review of Literature and Formulation of Standardised Indentation Toughness Equations. Materials Science and Technology, Vol. 5, 865–72.

Ponton, C. B. and Rawlings, R. D., 1989b. Vickers Indentation Fracture Toughness Test, Part 2. Application and Critical Evaluation of Standardised Indentation Toughness Equations. Materials Science and Technology, Vol. 5, 961–76.

Pawley, J. B., 1995. Handbook of Biological Confocal Microscopy. 2nd edition, New York: Plenum Press.

Selçuk, A. and Atkinson, A., 2000. Strength and Toughness of Tape-Cast Yttria-Stabilized Zirconia. Journal of the American Ceramic Society, Vol. 83[8], 2029–35 (2000).

Smith, W. J., 1966. Modern Optical Engineering. pp. 135–141, McGraw-Hill.

The invention claimed is:

1. A method for visualizing sub-micron size particles using a polarizing microscope comprising:

projecting a focused beam of polarized light onto a rotating target;

blocking a portion of the focused beam of polarized light from reaching the target with a blocking element;

producing a shadow region with a frame edge positioned in a field of view of the polarizing microscope; and diffracting light from the target onto the shadow region.

2. The method as claimed in claim 1, wherein half of the polarized light is blocked by the frame edge.

3. The method as claimed in claim 1, wherein two orthogonal light beams are directed onto said target, and superimposed light diffracted from said target is projected onto the shadow region.

4. The method as claimed in claim 1, wherein the target comprises a microstructure or crack and wherein the microstructure or crack diffracts light into the shadow region.

5. The method as claimed in claim 1, wherein the target comprises a sub-micron size particle.

6. The method as claimed in claim 5, wherein the sub-micron size particle comprises a biological particle.

7. The method as claimed in claim 5, wherein the sub-micron size particle is selected from the group consisting of mold, dust and a weaponized bio-agent.

8. The polarizing microscope as claimed in claim 1, further comprising a rotating stage for supporting the target.

9. A polarizing microscope for practicing the method of claim 1, said microscope having a condenser lens and an objective lens with a rotating target stage for rotatably supporting a target located at a focal point of the condenser lens, and a blocking element for blocking a portion of illuminating light up stream of the condenser lens.

10. The polarizing microscope as claimed in claim 9, wherein the blocking element is adapted to obstruct half of the illuminating light.

11. The polarizing microscope as claimed in claim 9, wherein the blocking element comprises a frame edge positioned in the polarizing microscope field of view.

* * * * *